(12) United States Patent
Ahn (10) Patent No.: US 11,026,724 B2
(45) Date of Patent: Jun. 8, 2021

(54) FIXING ROD CONNECTING DEVICE

(71) Applicants: Kyoung Gee Ahn, Seoul (KR); GBS Commonwealth Co., Ltd., Seoul (KR); PMT Republic, Inc., Walnut, CA (US)

(72) Inventor: Kyoung Gee Ahn, Seoul (KR)

(73) Assignees: Kyoung Gee Ahn, Seoul (KR); GBS Commonwealth Co., Ltd., Seoul (KR); PMT Republic, Inc., Walnut, CA (US)

( * ) Notice: Subject to any disclaimer, the term of this patent is extended or adjusted under 35 U.S.C. 154(b) by 90 days.

(21) Appl. No.: 16/465,356

(22) PCT Filed: Nov. 9, 2017

(86) PCT No.: PCT/KR2017/012634
§ 371 (c)(1),
(2) Date: May 30, 2019

(87) PCT Pub. No.: WO2018/101633
PCT Pub. Date: Jun. 7, 2018

(65) Prior Publication Data
US 2019/0388125 A1    Dec. 26, 2019

(30) Foreign Application Priority Data

Dec. 2, 2016 (KR) .................. 10-2016-0163302

(51) Int. Cl.
*A61B 17/70* (2006.01)
*A61B 17/86* (2006.01)

(52) U.S. Cl.
CPC .......... *A61B 17/7049* (2013.01); *A61B 17/86* (2013.01); *A61B 17/7002* (2013.01)

(58) Field of Classification Search
CPC ....................................... A61B 17/7049–7052
USPC .................................................. 606/260, 278
See application file for complete search history.

(56) References Cited

U.S. PATENT DOCUMENTS

| | | |
|---|---|---|
| 8,075,594 B2 | 12/2011 | Purcell |
| 8,998,961 B1 * | 4/2015 | Ziemek .................. A61B 17/86 606/278 |
| 10,390,863 B2 * | 8/2019 | Kim .................... A61B 17/7049 |
| 10,517,647 B2 * | 12/2019 | Lee ..................... A61B 17/7049 |
| 10,624,679 B2 * | 4/2020 | Murray .............. A61B 17/7032 |

(Continued)

FOREIGN PATENT DOCUMENTS

| | | |
|---|---|---|
| JP | 2012-501761 A | 1/2012 |
| KR | 10-0893918 B1 | 4/2009 |

(Continued)

*Primary Examiner* — Nicholas J Plionis
(74) *Attorney, Agent, or Firm* — Novick, Kim & Lee, PLLC; Jae Yoon Kim (57) ABSTRACT

The present invention relates to a fixing rod connecting device and, more specifically, to a fixing rod connecting device, comprising: a main body having a space into which one or more rods can be inserted; and a fixing screw fastened to the main body so as to fix the rod, wherein one side surface of the main body is formed to have a predetermined upward inclination angle relative to the other side surface thereof, thereby eliminating interference with other surgical instruments when the fixing screw is fastened, enabling an incision area of a patient to be minimized, and enabling three-dimensional alignment and fixation of the rod.

14 Claims, 11 Drawing Sheets

(56) References Cited

U.S. PATENT DOCUMENTS

| | | | |
|---|---|---|---|
| 2003/0028191 A1* | 2/2003 | Shluzas | A61B 17/7035 606/278 |
| 2003/0212398 A1* | 11/2003 | Jackson | A61B 17/7049 606/300 |
| 2005/0228378 A1* | 10/2005 | Kalfas | A61B 17/705 606/252 |
| 2006/0058787 A1* | 3/2006 | David | A61B 17/7041 606/256 |
| 2006/0079892 A1* | 4/2006 | Roychowdhury | A61B 17/7044 606/253 |
| 2006/0241602 A1* | 10/2006 | Jackson | A61B 17/7049 606/251 |
| 2007/0123860 A1* | 5/2007 | Francis | A61B 17/7049 606/250 |
| 2007/0270817 A1* | 11/2007 | Rezach | A61B 17/705 606/252 |
| 2008/0215095 A1* | 9/2008 | Biedermann | A61B 17/7037 606/246 |
| 2013/0261668 A1* | 10/2013 | Douget | A61B 17/7053 606/278 |
| 2014/0277160 A1* | 9/2014 | Ziolo | A61B 17/7049 606/278 |
| 2015/0119941 A1* | 4/2015 | Daniels | A61B 17/7056 606/270 |
| 2016/0338743 A1 | 11/2016 | Iott et al. | |
| 2017/0281245 A1* | 10/2017 | Murray | A61B 17/7049 |
| 2017/0333087 A1* | 11/2017 | Lee | A61B 17/7049 |
| 2017/0333088 A1* | 11/2017 | Lee | A61B 17/7049 |
| 2018/0228518 A1* | 8/2018 | Carruth | A61B 17/7032 |
| 2018/0243009 A1* | 8/2018 | Bobbitt | A61B 17/7049 |

FOREIGN PATENT DOCUMENTS

| | | |
|---|---|---|
| KR | 10-2010-0120072 A | 11/2010 |
| KR | 10-2015-0106627 A | 9/2015 |
| KR | 10-1567593 B1 | 11/2015 |

\* cited by examiner

FIG. 1

PRIOR ART

FIXING ROD CONNECTING DEVICE

TECHNICAL FIELD

The present invention relates to a fixing rod connecting device, and more particularly to a fixing rod connecting device that has a predetermined upward inclination angle in consideration of the anatomical shape of bones so as to avoid interference with surgical instruments and minimize the size of an incision during surgery and that enables a rod to be appropriately placed in three dimensions and to be fixed using a chuck.

BACKGROUND ART

In general, degenerative vertebral disease or vertebral deformity, such as degenerative disc disease, spinal stenosis, and spondylolisthesis, requires surgical treatment if there is no improvement after conservative treatment. As surgical treatment, spinal fixation is performed in the order of decompression, bone fusion, and fixation of a spine after the completion of bone fusion.

A commonly used spinal fixation treatment is performed such that a plurality of bone screws is fastened into vertebrae and connected to rods, which are disposed substantially parallel to the longitudinal direction of the spine, and such that a fixing rod connecting device is used to interconnect and support the two rods, thereby increasing the rigidity and stability of the entire assembly.

Figure 1:
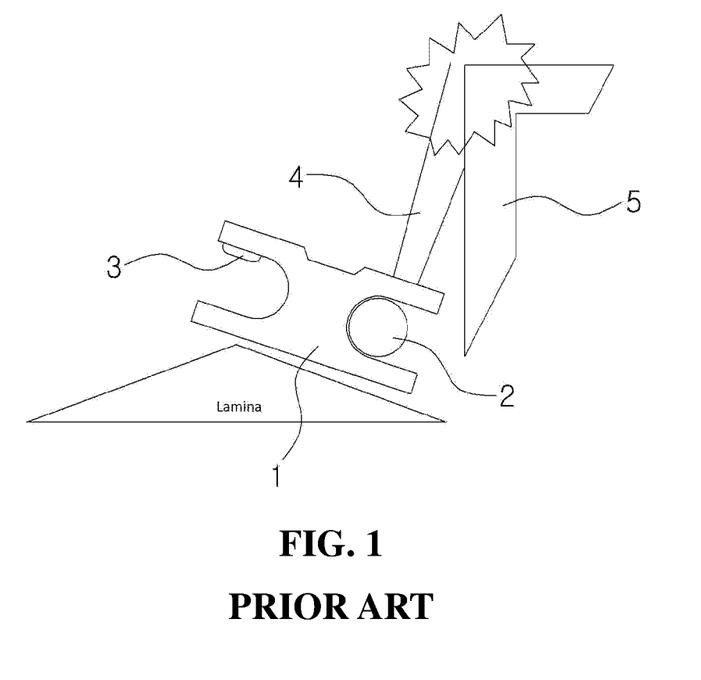
FIG. 1 is a view illustrating the appearance of a conventional fixing rod connecting device.

FIG. 1 is a view illustrating the appearance of a conventional fixing rod connecting device.

As illustrated, a conventional fixing rod connecting device includes a main body 1, which has therein spaces into which a pair of rods 2 is inserted, and fixing screws 3, which are fastened into the main body 1 in order to fix the rods 2.

The conventional fixing rod connecting device is formed so as to have an H-shaped cross-section, and thus a pair of rods is fixed parallel to each other. However, in an actual surgical procedure, a pair of rods is rarely placed geometrically parallel to each other. Thus, the conventional fixing rod connecting device has a directional limitation in fixing the rods that are placed in a body in three dimensions.

Further, the conventional fixing rod connecting device is designed without taking into account the anatomical characteristics of bones, and thus is placed at an incline on a slope of the spine, e.g. on a lamina. Thus, during surgery, a fastening tool 4 for use in the conventional fixing rod connecting device interferes with peripheral soft tissues or other surgical instruments 5 such as a retractor, which requires a large incision in a patient.

Furthermore, in order to overcome the above limitations, fixing rod connecting devices capable of being directionally used have been developed. However, such directionally usable fixing rod connecting devices include a plurality of parts that needs to be assembled and controlled during surgery, which leads to an increase in operation time.

Therefore, there is growing demand for a fixing rod connecting device that is suitable for fixing rods placed in a body in three dimensions, that does not interfere with other surgical instruments and thus enables minimization of the size of an incision, and that is easily fastened even during surgery.

The information disclosed in this Background of the Invention section is only for enhancement of understanding of the general background of the invention and should not be taken as an acknowledgement or any form of suggestion that this information forms the prior art already known to a person skilled in the art.

DISCLOSURE

Technical Problem

Therefore, the present invention has been made in view of the above problems, and it is an object of the present invention to provide a fixing rod connecting device in which one side of a main body has an upward inclination angle with respect to the other side thereof, thereby preventing interference between a fastening tool fastening a fixing screw and other surgical instruments and minimizing the size of an incision that is to be made in a patient.

It is another object of the present invention to provide a fixing rod connecting device that enables a rod to spherically rotate using a spherical-shaped chuck inserted into a receiving portion so that the rod is appropriately placed in three dimensions and is then fixed and that includes a main body formed in an integral type so as to facilitate fastening work during surgery.

However, the objects to be accomplished by the invention are not limited to the above-mentioned objects, and other objects not mentioned will be clearly understood by those skilled in the art from the following description.

Technical Solution

In accordance with the present invention, the above and other objects can be accomplished by the provision of a fixing rod connecting device including a main body having a space formed therein to allow at least one rod to be inserted thereinto, and a fixing screw configured to be fastened into the main body in order to fix the rod, wherein one side of the main body is formed so as to have a predetermined upward inclination angle with respect to the opposite side of the main body.

In addition, in the fixing rod connecting device according to the embodiment of the present invention, the main body may be formed in an integral type, and a pair of rods may be inserted into both sides of the main body so as to be disposed at different heights from each other with respect to the lower end portion of the main body.

In addition, in the fixing rod connecting device according to the embodiment of the present invention, the axis passing through the center of the fixing screw fastened into the main body and the lower end portion of the main body may form an insertion angle of 90° or less therebetween.

In addition, in the fixing rod connecting device according to the embodiment of the present invention, a pair of fixing screws may be fastened into the main body, and the axes passing through the centers of the pair of fixing screws may form an angle less than 90° therebetween.

In addition, the fixing rod connecting device according to the embodiment of the present invention may further include a receiving portion formed in at least one side of the main body in order to surround the outer circumferential surface of the rod, and a chuck configured to be inserted into the receiving portion, the chuck being disposed between the outer circumferential surface of the rod and the inner circumferential surface of the receiving portion.

In addition, in the fixing rod connecting device according to the embodiment of the present invention, the chuck may have a plurality of slits formed in the circumferential surface thereof so as to be elastically deformed.

In addition, in the fixing rod connecting device according to the embodiment of the present invention, some of the slits formed in the circumferential surface of the chuck may extend from the upper end of the chuck toward the center of the chuck, and the remaining ones of the slits may extend from the lower end of the chuck toward the center of the chuck.

In addition, in the fixing rod connecting device according to the embodiment of the present invention, the slits extending from the upper end of the chuck to the center of the chuck and the slits extending from the lower end of the chuck to the center of the chuck may be alternately arranged along the circumferential surface of the chuck.

In addition, in the fixing rod connecting device according to the embodiment of the present invention, the chuck may include restraining portions protruding from both ends thereof, and the restraining portions may be held in contact with the inner circumferential surface of the receiving portion.

In addition, in the fixing rod connecting device according to the embodiment of the present invention, the fixing screw may be formed to have a tapered shape or a round shape in which the diameter of the fixing screw gradually decreases toward the distal end of the fixing screw so as to contact the outer circumferential surface of the rod.

In addition, in the fixing rod connecting device according to the embodiment of the present invention, the main body may have a pair of space portions formed in both sides thereof to allow a pair of rods to be inserted thereinto, and the pair of space portions may be formed as open portions, each of the open portions having an open part through which a part of the outer circumferential surface of a corresponding one of the rods is exposed to the outside.

In addition, in the fixing rod connecting device according to the embodiment of the present invention, the main body may have a pair of space portions formed in both sides thereof to allow a pair of rods to be inserted thereinto, one of the pair of space portions may be formed as an open portion, the open portion having an open part through which a part of the outer circumferential surface of a corresponding one of the rods is exposed to the outside, and the remaining one of the pair of space portions may be formed as a receiving portion, the receiving portion being formed in a closed type so as to surround the outer circumferential surface of a corresponding one of the rods.

In addition, in the fixing rod connecting device according to the embodiment of the present invention, the main body may have a pair of space portions formed in both sides thereof to allow a pair of rods to be inserted thereinto, and the pair of space portions may be formed as receiving portions, the receiving portions being formed in a closed type so as to surround the outer circumferential surfaces of the rods.

In addition, in the fixing rod connecting device according to the embodiment of the present invention, when each of the space portions is formed as a receiving portion surrounding the outer circumferential surface of a corresponding one of the rods, a chuck may be disposed between the outer circumferential surface of a corresponding one of the rods and the inner circumferential surface of the receiving portion.

In addition, in the fixing rod connecting device according to the embodiment of the present invention, when each of the space portions is formed as a receiving portion surrounding the outer circumferential surface of a corresponding one of the rods, the fixing screw may be fastened into the main body so as not to expose the distal end of the fixing screw to the outside from the receiving portion.

Advantageous Effects

In the present invention constructed as described above, since one side of the main body has an upward inclination angle with respect to the other side thereof, the insertion angle of the fixing screw is an acute angle, whereby a fastening tool fastening the fixing screw may not interfere with other surgical instruments, and the size of an incision that is to be made in a patient during surgery may be minimized.

In addition, since the main body having a predetermined inclination angle is formed in an integral type, there are few parts that need to be assembled and controlled during surgery, whereby the operation of the device of the present invention may be simplified, fastening work may be facilitated, and an operation time may be shortened.

In addition, since the rod is capable of spherically rotating due to the spherical-shaped chuck inserted into the receiving portion, a pair of rods may be appropriately placed to a certain extent in three dimensions and may then be fixed in accordance with the actual surgery situation.

In addition, since the slits formed in the spherical-shaped chuck are machined in both directions of the chuck, the chuck may be evenly deformed when pressed by the fixing screw. Since the distal end of the fixing screw is formed in a tapered or round shape, the contact area with the rod may be increased.

BEST MODE

A fixing rod connecting device according to the present invention includes a main body having a space formed therein to allow at least one rod to be inserted thereinto, and a fixing screw configured to be fastened into the main body in order to fix the rod, wherein one side of the main body is formed so as to have a predetermined upward inclination angle with respect to the opposite side of the main body.

MODE FOR INVENTION

Hereinafter, embodiments of the present invention will be described in detail with reference to the accompanying drawings so that those skilled in the art can easily carry out the embodiments. The present invention may, however, be embodied in many different forms, and should not be construed as being limited to the embodiments set forth herein.

In order to clearly explain the present invention, illustration of elements having no connection with the description is omitted, and the same or similar elements are designated by the same reference numerals throughout the specification.

Further, it is to be understood that the phraseology and terminology used in the following specification and appended claims should not be construed as being limited to general or dictionary meanings but should be construed as having meanings and concepts according to the spirit of the present invention on the basis of the principle that the inventor is permitted to define appropriate terms for the best explanation.

Figure 2:
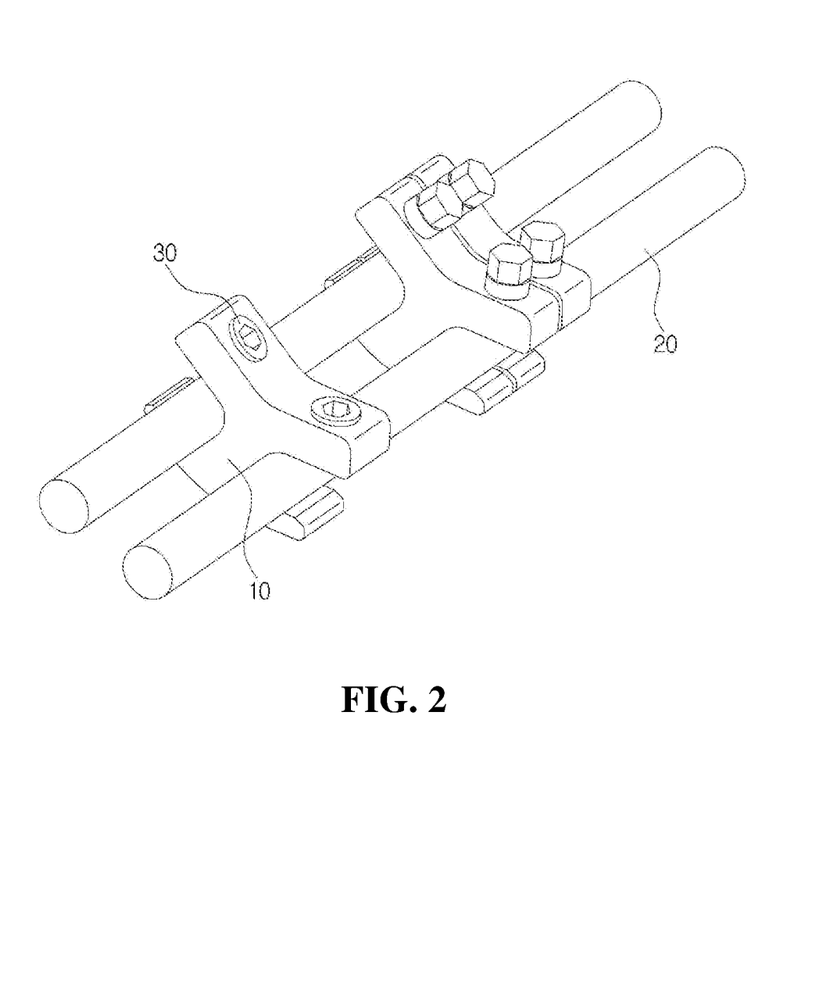
FIG. 2 is a perspective view illustrating the appearance of a fixing rod connecting device according to an embodiment of the present invention.
Figure 3:
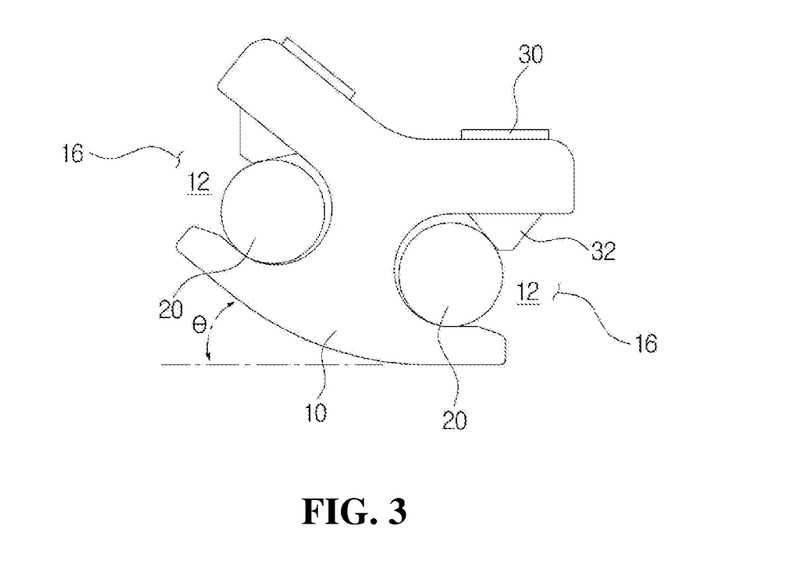
FIG. 3 is a front view illustrating the appearance of the fixing rod connecting device according to the embodiment of the present invention.
Figure 4:
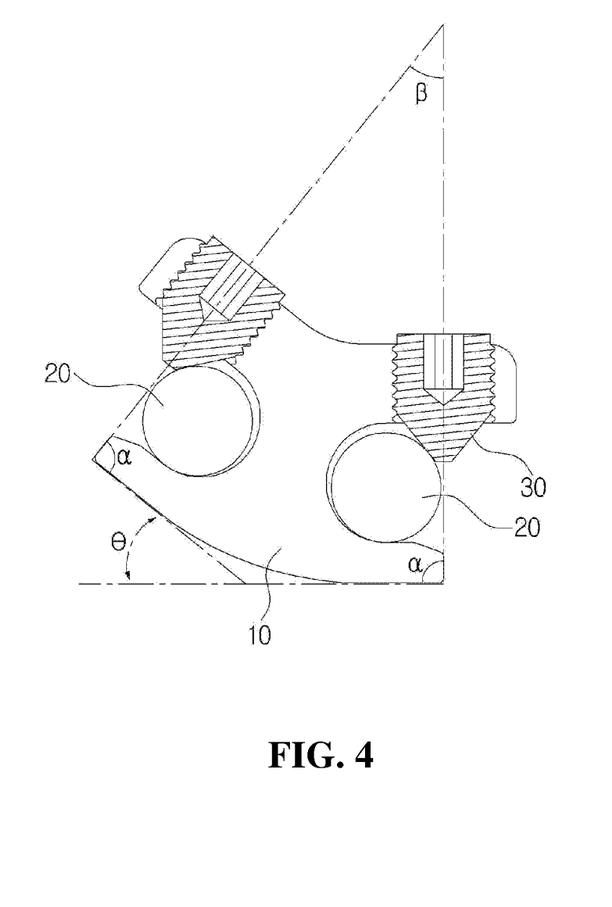
FIG. 4 is a cross-sectional view illustrating the appearance of the fixing rod connecting device according to the embodiment of the present invention.

FIG. 2 is a perspective view illustrating the appearance of a fixing rod connecting device according to an embodiment of the present invention, FIG. 3 is a front view illustrating the appearance of the fixing rod connecting device according to the embodiment of the present invention, and FIG. 4 is a cross-sectional view illustrating the appearance of the fixing rod connecting device according to the embodiment of the present invention.

As illustrated, the fixing rod connecting device according to the present invention includes a main body 10 having a space formed therein to allow at least one rod 20 to be inserted thereinto, and a fixing screw 30 configured to be fastened into the main body 10 in order to fix the rod 20.

The rod 20 interconnects a plurality of bone screws (not illustrated) secured to bones such as injured vertebrae. Each of the bone screws has screw threads formed in the outer circumferential surface thereof, so as to be fastened into a bone, and a spherical-shaped head formed at one end portion thereof.

The rod 20 is disposed substantially parallel to the longitudinal direction of the spine. Two rods 20 may be interconnected and supported by the main body 10 and the fixing screw 30, thereby increasing the rigidity and stability of the entire assembly and fixing long segments of the spine.

The main body 10 is formed of a material that does not corrode in a body and that is suitable for robustly supporting the rod 20. For example, the main body 10 may be formed of a medical material such as a titanium (Ti) alloy, a cobalt-chromium (Co—Cr) alloy, a stainless-steel alloy, a natural resin, or a synthetic resin.

Further, it is preferable that one side of the lower end of the main body 10 (the left side in the illustrated embodiment) be formed so as to have a predetermined upward inclination angle $\theta$ with respect to the opposite side thereof (the right side in the illustrated embodiment).

The inclination angle $\theta$ of the main body 10 may be determined in consideration of the anatomical shape of the spine and the like, whereby interference with surgical instruments may be prevented, and the size of an incision that is to be made in a patient during surgery may be minimized.

Unlike the conventional fixing rod connecting device, the main body 1 of which is simply formed in an H-shape as illustrated in FIG. 1, the present invention is characterized in that the main body 10 has the upward inclination angle $\theta$.

Here, the main body 10 may be formed in an integral type, rather than a type in which a plurality of parts is combined, such that a pair of rods 20 is inserted into both sides of the main body 10, and the rods 20 inserted into the main body 10 may be disposed at different heights from each other with respect to the lower end portion of the main body 10.

That is, the pair of rods 20 may be disposed in different virtual planes from each other with respect to the ground, and the main body 10 is formed in a simple shape, thus simplifying the operation of the device and facilitating fastening work during surgery, and consequently shortening an operation time.

As illustrated in FIG. 4, the axis passing through the center of the fixing screw 30 fastened into the main body 10 (indicated by the alternating long and short dashed line in the drawing) and the lower end portion of the main body 10 may form an insertion angle $\alpha$, which is equal to or less than 90°, therebetween.

Accordingly, when the left side of the lower end portion of the main body 10 is brought into contact with the spine (e.g. the lamina shown in FIG. 1), the fixing screw 30 disposed on the right side of the main body may be fastened at the insertion angle $\alpha$, which is a substantially right angle.

Since the insertion angle a of the fixing screw 30 is a right angle or an acute angle, a fastening tool such as a screwdriver for rotating the fixing screw does not interfere with other surgical instruments such as a retractor.

Further, a pair of fixing screws 30 may be fastened into the main body 10, and the axes passing through the centers of the pair of fixing screws (indicated by the alternating long and short dashed lines in the drawing) form an angle $\beta$, which is less than 90°, therebetween.

Since an acute angle is formed between the pair of fixing screws 30, a user may fasten the fixing screws 30 into the main body 10 using a fastening tool with a minimum motion, and the size of an incision may be further minimized during surgery.

Figure 5:
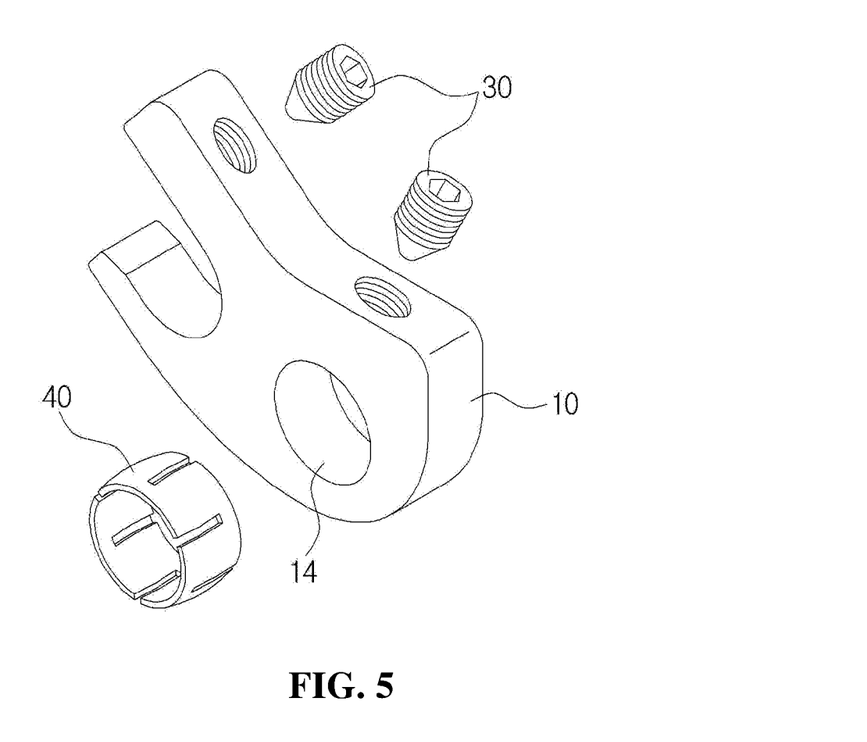
FIG. 5 is an exploded perspective view illustrating the appearance of a fixing rod connecting device according to another embodiment of the present invention.
Figure 6:
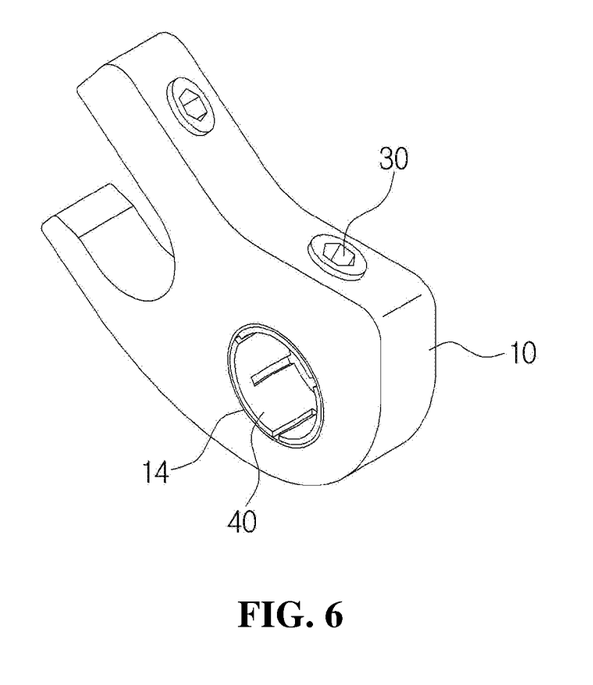
FIG. 6 is a view illustrating the assembled appearance of the fixing rod connecting device according to the other embodiment of the present invention.
Figure 7:
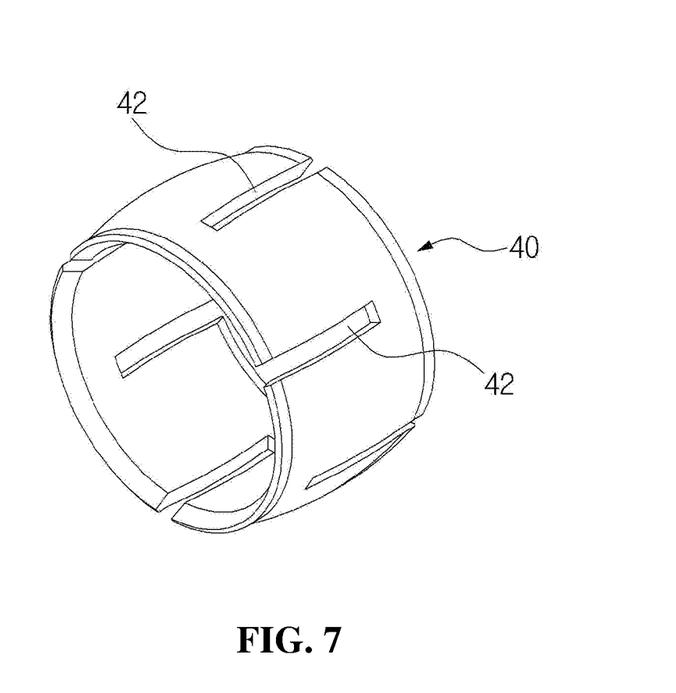
FIG. 7 is a perspective view illustrating the appearance of a chuck according to the other embodiment of the present invention.
Figure 8:
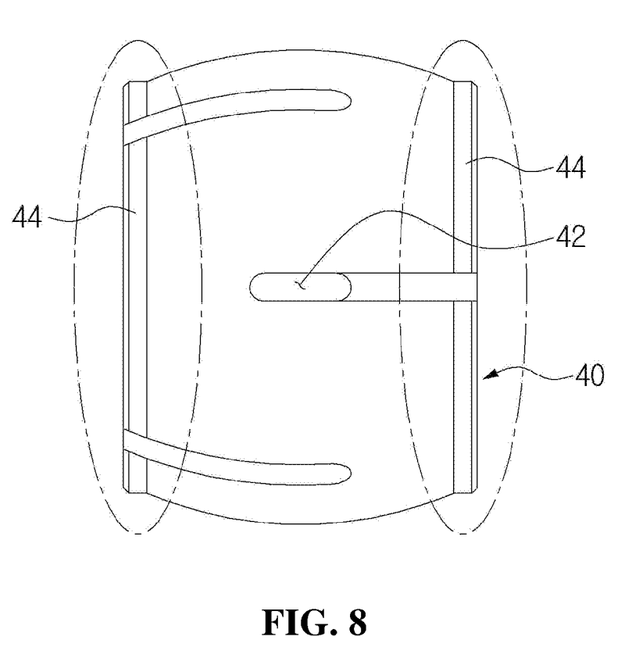
FIG. 8 is a front view illustrating the appearance of the chuck according to the other embodiment of the present invention.
Figure 9:
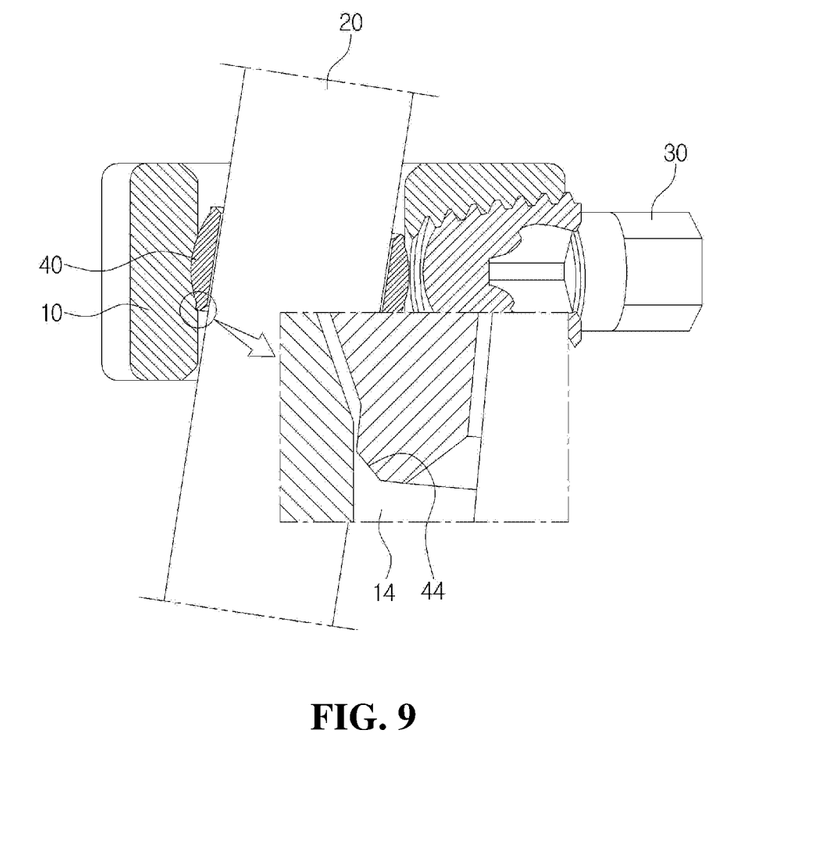
FIG. 9 shows a cross-sectional view and an enlarged view illustrating the appearance of the fixing rod connecting device according to the other embodiment of the present invention.

FIG. 5 is an exploded perspective view illustrating the appearance of a fixing rod connecting device according to another embodiment of the present invention, FIG. 6 is a view illustrating the assembled appearance of the fixing rod connecting device according to the other embodiment of the present invention, FIG. 7 is a perspective view illustrating the appearance of a chuck according to the other embodiment of the present invention, FIG. 8 is a front view illustrating the appearance of the chuck according to the other embodiment of the present invention, and FIG. 9 shows a cross-sectional view and an enlarged view illustrating the appearance of the fixing rod connecting device according to the other embodiment of the present invention.

As illustrated, the main body 10 has a receiving portion 14 formed in one side or both sides of the main body 10 in a circular, elliptical or oval shape so as to surround the outer circumferential surface of the rod 20, and a spherical chuck 40 is inserted into the receiving portion 14 so as to be disposed between the outer circumferential surface of the rod 20 and the inner circumferential surface of the receiving portion 14.

That is, the chuck 40, the receiving portion 14 and the main body 10 are arranged in that order on the outer circumference of the rod 20, and the rod 20 is secured in the receiving portion 14 by the fixing screw 30 pressing the chuck 40 and the rod 20.

In addition, a plurality of slits 42 is formed in the circumferential surface of the chuck 40. The slits 42 are formed so as to extend in the longitudinal direction of the chuck 40 and are arranged in the circumferential direction of the chuck 40. The slits 42 provide elastic deformation force to the chuck when the chuck 40 is inserted into the receiving portion 14.

Specifically, it is preferable that some of the slits 42 extend from the upper end of the chuck 40 toward the center of the chuck 40 and that the remaining ones of the slits 42 extend from the lower end of the chuck 40 toward the center of the chuck 40.

That is, the slits 42 formed in the chuck 40 are machined in both directions of the chuck 40, thereby serving to induce the chuck to be evenly deformed when the fixing screw 30 presses the chuck 40.

It is preferable that the slits 42 extending from the upper end of the chuck 40 to the center of the chuck 40 and the slits 42 extending from the lower end of the chuck 40 to the center of the chuck 40 be alternately arranged along the circumference of the chuck 40. In some cases, however, it will be appreciated by those skilled in the art that the slits may be formed in various other arrangements in consideration of the degree to which the chuck is pressed, the material of the chuck, the force required to fix the rod, and the like.

Meanwhile, it is preferable that restraining portions 44 protrude from both ends (the upper and lower ends) of the chuck 40. The restraining portions 44 extend at a predetermined angle from the chuck 40, and are held in contact with the inner circumferential surface of the receiving portion 14 so that the rod 20 may spherically rotate within a predetermined angle.

As illustrated in FIG. 9, the restraining portions 44 are held in contact with the inner circumferential surface of the receiving portion 14 before the rod 20 is brought into contact with the main body 10, thereby restricting the angles within which the chuck 40 and the rod 20 move. Thus, the rod 20 may be appropriately placed in three dimensions and may then be fixed.

As illustrated in FIG. 3, the fixing screw 30 may be formed to have a tapered shape or a round shape in which the diameter thereof gradually decreases toward the distal end 32 thereof so as to contact the outer circumferential surface of the rod 20 and fix the rod.

Since the distal end 32 of the fixing screw 30 is the portion that directly contacts the rod 20, the contact area between the fixing screw 30 and the rod 20 may be maximized due to the distal end having the above shape. Of course, the distal end 32 of the fixing screw 30 may formed in various other shapes depending on a change in the shape of the rod, the contact area between the rod and the fixing screw, and the like.

The fixing screw 30 may have a tool recess formed in the upper end thereof, into which a screwdriver is fitted in order to rotate the fixing screw, or may have an angled nut formed at the upper end thereof so as to be rotated by a wrench or the like.

Figure 10:
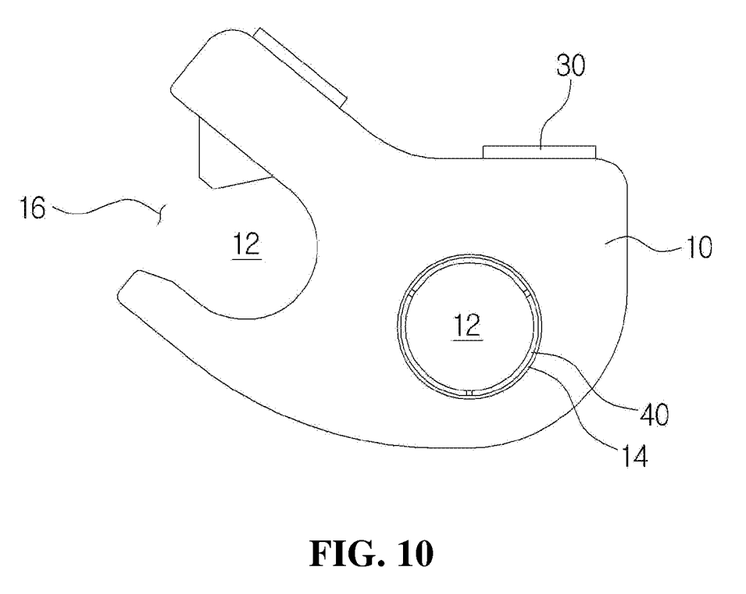
FIG. 10 is a front view illustrating the appearance of the fixing rod connecting device according to the other embodiment of the present invention.
Figure 11:
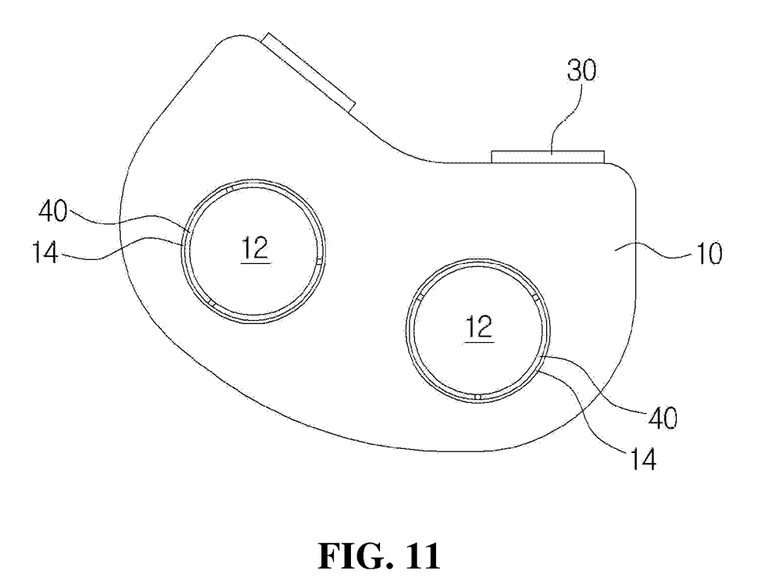
FIG. 11 is a front view illustrating the appearance of a fixing rod connecting device according to still another embodiment of the present invention.

FIG. 10 is a front view illustrating the appearance of the fixing rod connecting device according to another embodiment of the present invention, and FIG. 11 is a front view illustrating the appearance of a fixing rod connecting device according to still another embodiment of the present invention.

As illustrated in FIG. 3, the main body 10 may have a pair of space portions 12 formed in both sides thereof to allow a pair of rods 20 to be inserted thereinto, and the pair of space portions 12 may be formed as open portions 16, a part of each of which is open so that a part of the outer circumferential surface of a corresponding one of the rods 20 is exposed to the outside.

Alternatively, as illustrated in FIG. 10, one of the pair of space portions 12 may be formed as an open portion 16, a part of which is open so that a part of the outer circumferential surface of a corresponding one of the rods 20 is exposed to the outside, and the other one thereof may be formed as a receiving portion 14, which is formed in a closed type so as to surround the outer circumferential surface of a corresponding one of the rods 20.

Alternatively, as illustrated in FIG. 11, the pair of space portions 12 may be formed as receiving portions 14, which are formed in a closed type so as to surround the outer circumferential surfaces of the rods 20.

That is, the main body 10 may be formed such that the pair of space portions 12 is formed in an open type, such that one of the pair of space portions is formed in an open type and the other one thereof is formed in a closed type, or such that the pair of space portions is formed in a closed type. In this manner, the main body may be formed in various configurations in consideration of the surgery circumstances, the body condition of a patient, and the like.

Here, in the case in which the space portion 12 is formed as the receiving portion 14 surrounding the outer circumferential surface of the rod 20, it is preferable for the chuck 40 to be disposed between the outer circumferential surface of the rod 20 and the inner circumferential surface of the receiving portion 14 and for the fixing screw 30 to be fastened into the main body 10 so as not to expose the distal end 32 of the fixing screw 30 to the outside from the receiving portion 14.

In the present invention constructed as described above, since one side of the main body 10 has an upward inclination angle with respect to the other side thereof, the insertion angle of the fixing screw 30 is an acute angle, whereby a fastening tool fastening the fixing screw may not interfere with other surgical instruments, and the size of an incision that is to be made in a patient during surgery may be minimized.

In addition, since the main body 10 having a predetermined inclination angle is formed in an integral type, there are few parts that need to be assembled and controlled during surgery, whereby the operation of the device of the present invention may be simplified, fastening work may be facilitated, and an operation time may be shortened.

In addition, since the rod 20 is capable of spherically rotating due to the spherical-shaped chuck 40 inserted into the receiving portion 14, a pair of rods may be appropriately placed to a certain extent in three dimensions and may then be fixed in accordance with the actual surgery situation.

In addition, since the slits 42 formed in the spherical-shaped chuck 40 are machined in both directions of the chuck 40, the chuck may be evenly deformed when pressed by the fixing screw 30. Since the distal end 32 of the fixing screw 30 is formed in a tapered or round shape, the contact area with the rod 20 may be increased.

While the present invention has been particularly described with reference to exemplary embodiments and accompanying drawings, the present invention is not limited thereto, and it will be apparent to those skilled in the art that various modifications and applications may be made without departing from the spirit and scope of the present invention as defined in the following claims.

The invention claimed is:

1. A fixing rod connecting device comprising:
   a main body having an upper surface and a lower surface opposite to the upper surface, and having a pair of space portions formed on both sides of the main body between the upper surface and the lower surface to allow a pair of rods to be inserted thereinto; and
   a pair of fixing screws configured to be fastened into the main body through a pair of holes formed on the upper surface of the main body in order to fix the pair of rods,
   wherein a first area of the lower surface of the main body is formed to have a predetermined upward inclination angle with respect to an opposite side a second area of the lower surface of the main body, the first area of the lower surface being extended from a first edge of the lower surface and the second area of the lower surface being extended from a second edge of the lower surface, the first edge and the second edge of the lower surface being positioned opposite to each other,
   wherein a first area of the upper surface of the main body is formed to have a predetermined upward inclination angle with respect to a second area of the upper surface of the main body, the first area of the upper surface being extended from a first edge of the upper surface and the second area of the upper surface being extended from a second edge of the upper surface, the first edge and the second edge of the upper surface being positioned opposite to each other, and
   wherein, when the pair of fixing screws are fastened into the main body, axes passing through centers of the pair of fixing screws and extending from tips of the pair of fixing screws toward tops of the pair of fixing screws intersect to form an angle less than 90° therebetween.

2. The fixing rod connecting device according to claim 1, wherein the main body is integrally formed, and
   wherein, when the pair of rods are inserted into the pair of space portions, the pair of rods are disposed at different heights from each other with respect to a lower end portion of the main body.

3. The fixing rod connecting device according to claim 1, wherein one of the axes passing through the centers of the pair of fixing screws fastened into the main body and a lower end portion of the main body form an insertion angle of 90° or less therebetween.

4. The fixing rod connecting device according to claim 1, wherein the pair of space portions includes a receiving portion formed in at least one side of the main body to surround an outer circumferential surface of the rod inserted thereinto, and
   wherein the fixing rod connecting device further comprises a chuck configured to be inserted into the receiving portion, the chuck being disposed between the outer circumferential surface of the rod and an inner circumferential surface of the receiving portion.

5. The fixing rod connecting device according to claim 4, wherein the chuck has a plurality of slits formed in a circumferential surface thereof so as to be elastically deformed.

6. The fixing rod connecting device according to claim 5, wherein some of the plurality of slits formed in the circumferential surface of the chuck extend from an upper end of the chuck toward a center of the chuck, and remaining ones of the plurality of slits extend from a lower end of the chuck toward the center of the chuck.

7. The fixing rod connecting device according to claim 6, wherein the slits extending from the upper end of the chuck to the center of the chuck and the slits extending from the lower end of the chuck to the center of the chuck are alternately arranged along the circumferential surface of the chuck.

8. The fixing rod connecting device according to claim 4, wherein the chuck comprises restraining portions protruding from both ends thereof, and
   wherein the restraining portions are held in contact with the inner circumferential surface of the receiving portion.

9. The fixing rod connecting device according to claim 1, wherein each of the pair of fixing screws has a tapered shape or a round shape in which a diameter of the fixing screw gradually decreases toward a distal end of the fixing screw so as to contact an outer circumferential surface of the rod fixed by each of the pair of fixing screws.

10. The fixing rod connecting device according to claim 1,
    wherein the pair of space portions are formed to be open, and each of the pair of space portions having an open part through which a part of an outer circumferential surface of the rod inserted thereinto is exposed to an outside.

11. The fixing rod connecting device according to claim 1,
    wherein one of the pair of space portions is formed to be open and has an open part through which a part of an outer circumferential surface of the rod inserted thereinto is exposed to an outside, and the other one of the pair of space portions is formed to be closed so as to surround an outer circumferential surface of the rod inserted thereinto.

12. The fixing rod connecting device according to claim 1,
    wherein the pair of space portions are formed to be closed so as to surround outer circumferential surfaces of the pair of rods inserted thereinto.

13. The fixing rod connecting device according to claim 12, wherein, when each of the space portions is formed to be closed for surrounding an outer circumferential surface of the rod inserted thereinto, a chuck is disposed between the outer circumferential surface of the rod inserted thereinto and an inner circumferential surface of the closed space portion.

14. The fixing rod connecting device according to claim 12, wherein, when each of the space portions is formed to be closed for surrounding an outer circumferential surface of the rod inserted thereinto, the fixing screw fastened for the rod inserted into the closed space portion is configured not to expose a distal end of the fixing screw to an outside from the closed space portion.

* * * * *